United States Patent
Harauchi et al.

(10) Patent No.: US 12,030,851 B2
(45) Date of Patent: Jul. 9, 2024

(54) PHENOL COMPOUND, RESIN COMPOSITION AND METHOD OF PRODUCING SAME, AND SHAPED PRODUCT

(71) Applicant: ZEON CORPORATION, Tokyo (JP)

(72) Inventors: Yosuke Harauchi, Tokyo (JP); Takashi Houkawa, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 428 days.

(21) Appl. No.: 17/597,702

(22) PCT Filed: Jul. 15, 2020

(86) PCT No.: PCT/JP2020/027523
§ 371 (c)(1),
(2) Date: Jan. 19, 2022

(87) PCT Pub. No.: WO2021/020133
PCT Pub. Date: Feb. 4, 2021

(65) Prior Publication Data
US 2022/0234986 A1     Jul. 28, 2022

(30) Foreign Application Priority Data
Jul. 31, 2019   (JP) .................................. 2019-141555

(51) Int. Cl.
| | | |
|---|---|---|
| C07C 69/54 | (2006.01) |
| C07C 39/08 | (2006.01) |
| C07C 39/12 | (2006.01) |
| C07C 39/15 | (2006.01) |
| C07C 39/16 | (2006.01) |
| C07C 39/21 | (2006.01) |
| C07C 69/732 | (2006.01) |
| C08F 8/04 | (2006.01) |
| C08F 20/20 | (2006.01) |
| C08K 5/134 | (2006.01) |
| C08L 101/00 | (2006.01) |

(52) U.S. Cl.
CPC .............. *C07C 69/54* (2013.01); *C07C 39/08* (2013.01); *C07C 39/12* (2013.01); *C07C 39/15* (2013.01); *C07C 39/16* (2013.01); *C07C 39/21* (2013.01); *C07C 69/732* (2013.01); *C08F 8/04* (2013.01); *C08F 20/20* (2013.01); *C08K 5/134* (2013.01); *C08L 101/00* (2013.01); *C08L 2201/08* (2013.01)

(58) Field of Classification Search
CPC ....... C07C 69/54; C07C 69/732; C07C 39/12; C07C 39/21; C07C 39/15; C07C 39/08; C07C 39/16; C08F 8/04; C08F 20/20; C08K 5/134; C08L 101/00; C08L 2201/08

See application file for complete search history.

(56) References Cited

U.S. PATENT DOCUMENTS 2,315,556 A * 4/1943 Soday ..................... C07C 37/18
568/744
7,084,196 B2    8/2006 Troutman et al.

FOREIGN PATENT DOCUMENTS

| CA | 2026900 A1 | 4/1991 |
| CN | 1498244 A | 5/2004 |
| EP | 0322166 A1 | 6/1989 |
| JP | H01168643 A | 7/1989 |
| JP | H03207788 A | 9/1991 |

OTHER PUBLICATIONS

Jul. 26, 2023, the Extended European Search Report issued by the European Patent Office in the corresponding European Patent Application No. 20847854.5.

Feb. 1, 2022, International Preliminary Report on Patentability issued in the International Patent Application No. PCT/JP2020/027523.

* cited by examiner

*Primary Examiner* — Patrick D Niland

(74) *Attorney, Agent, or Firm* — KENJA IP LAW PC

(57) ABSTRACT

Provided is a phenol compound represented by general formula (I), shown below. In general formula (I), $R^1$ and $R^2$ each indicate, independently of each other, a hydrogen atom or an alkyl group.

(I)

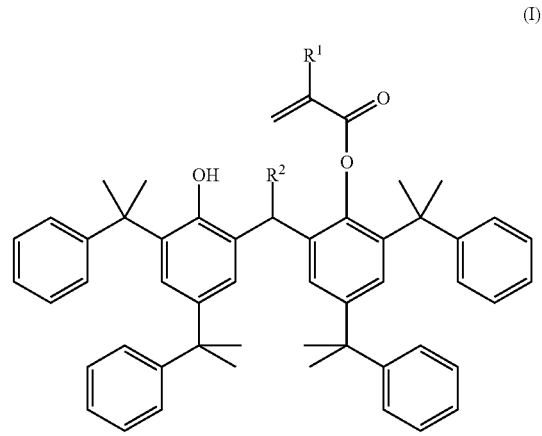

7 Claims, No Drawings

PHENOL COMPOUND, RESIN COMPOSITION AND METHOD OF PRODUCING SAME, AND SHAPED PRODUCT

TECHNICAL FIELD

The present disclosure relates to a phenol compound, a resin composition and method of producing the same, and a shaped product.

BACKGROUND

In production of a resin composition, a production process that involves heat treating a polymer solution containing a polymerization solvent under reduced pressure and high temperature conditions may be implemented. Since the polymer solution is normally treated at a temperature significantly higher than the boiling point of the polymerization solvent in this heat treatment with the aim of removing the polymerization solvent, the polymer that is obtained through the heat treatment may experience problems such as thermal degradation and coloring. For this reason, additives have been developed that, through addition thereof to a resin composition, can alleviate problems such as thermal degradation caused by heat treatment.

As one example, Patent Literature (PTL) 1 proposes a phenol compound that can prevent thermal degradation and coloring of a polymer such as when high temperature treatment is performed to remove a polymer from a polymer solution in production of a butadiene polymer.

CITATION LIST

Patent Literature

PTL 1: JP-H1-168643A

SUMMARY

Technical Problem

In a situation in which a resin (i.e., a polymer) is subjected to heat treatment under reduced pressure and high temperature conditions as described above during production of a resin composition, the polymer may decompose, resulting in thermal degradation of the polymer.

Consequently, there is need for an additive that can sufficiently inhibit decomposition of a resin even in a situation in which heat treatment is performed under reduced pressure and high temperature conditions during production of a resin composition. In order to achieve this, the additive not only needs to have inhibitive capability against resin decomposition but also needs to not readily volatilize itself even upon exposure to high temperature conditions.

However, the bisphenol monoacrylate compound described in PTL 1 and other commonly known additives either have insufficient inhibitive capability against resin decomposition under reduced pressure and high temperature conditions or readily volatilize under high temperature conditions.

Accordingly, one object of the present disclosure is to provide a phenol compound that does not readily volatilize even upon exposure to high temperature conditions and that has sufficiently high inhibitive capability against resin decomposition under reduced pressure and high temperature conditions.

Another object of the present disclosure is to provide a resin composition containing this phenol compound and a method of producing the resin composition.

Yet another object of the present disclosure is to provide a shaped product that is formed of the resin composition.

Solution to Problem

The inventors made extensive studies to solve the problem set forth above. The inventors reached a new discovery that a phenol compound satisfying a specific structure does not readily volatilize even upon exposure to high temperature conditions and has excellent inhibitive capability against resin decomposition under reduced pressure and high temperature conditions, and, in this manner, the inventors completed the present disclosure.

Specifically, the present disclosure aims to advantageously solve the problem set forth above, and a presently disclosed phenol compound is represented by general formula (I), shown below,

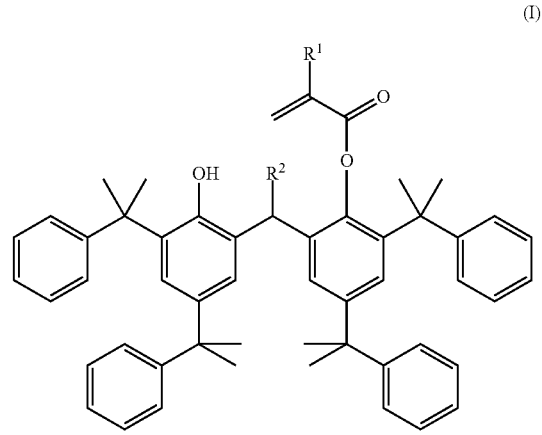

where, in general formula (I), $R^1$ and $R^2$ each indicate, independently of each other, a hydrogen atom or an alkyl group. A phenol compound that has the specific structure set forth above in this manner does not readily volatilize even upon exposure to high temperature conditions and has sufficiently high inhibitive capability against resin decomposition under reduced pressure and high temperature conditions. Therefore, compounding of this phenol compound in a resin composition makes it possible to sufficiently inhibit resin decomposition even in a situation in which the resin composition is subjected to treatment under reduced pressure and high temperature conditions.

In the presently disclosed phenol compound, it is preferable that $R^1$ and $R^2$ in general formula (I) are each a hydrogen atom. In other words, the presently disclosed phenol compound is preferably a bisphenol monoacrylate compound. Compounding of this bisphenol monoacrylate compound in a resin composition makes it possible to more sufficiently inhibit resin decomposition even in a situation in which the resin composition is subjected to treatment under reduced pressure and high temperature conditions.

In the presently disclosed phenol compound, it is preferable that $R^1$ in general formula (I) is a methyl group and $R^2$ in general formula (I) is a hydrogen atom. In other words, the presently disclosed phenol compound is preferably a bisphenol monomethacrylate compound. Compounding of this bisphenol monomethacrylate compound in a resin composition makes it possible to more sufficiently inhibit resin decomposition even in a situation in which the resin composition is subjected to treatment under reduced pressure and high temperature conditions.

Moreover, the present disclosure aims to advantageously solve the problem set forth above, and a presently disclosed resin composition comprises: a resin; and any one of the phenol compounds set forth above. The inclusion of at least any one of the phenol compounds set forth above in the resin composition makes it possible to sufficiently inhibit resin decomposition even in a situation in which the resin composition is subjected to treatment under reduced pressure and high temperature conditions.

In the presently disclosed resin composition, it is preferable that the resin is a thermoplastic polymer. By compounding a thermoplastic polymer as a resin and the phenol compound set forth above in combination in a resin composition, inhibitive capability against resin decomposition under reduced pressure and high temperature conditions can be more effectively displayed.

Furthermore, the present disclosure aims to advantageously solve the problem set forth above, and a presently disclosed shaped product is obtained through shaping of the resin composition set forth above. A shaped product that is obtained through shaping of the resin composition set forth above has excellent properties.

Also, the present disclosure aims to advantageously solve the problem set forth above, and a presently disclosed method of producing a resin composition comprises a heating step of heating a mixture containing the resin and the phenol compound to 200° C. or higher under reduced pressure. By performing depressurization and heating under specific conditions with respect to a mixture that contains a resin and the specific phenol compound, it is possible to efficiently produce a resin composition having good properties.

Note that the phrase "under reduced pressure" as used in the present specification means in an environment of 50 kPa or lower in terms of absolute pressure.

Advantageous Effect

According to the present disclosure, it is possible to provide a phenol compound that does not readily volatilize even upon exposure to high temperature conditions and that has sufficiently high inhibitive capability against resin decomposition under reduced pressure and high temperature conditions.

Moreover, according to the present disclosure, it is possible to provide a resin composition containing this phenol compound and an efficient production method for the resin composition.

Furthermore, according to the present disclosure, it is possible to provide a shaped product that is formed of the resin composition.

DETAILED DESCRIPTION

The following provides a detailed description of embodiments of the present disclosure.

The presently disclosed phenol compound does not readily volatilize even upon exposure to high temperature conditions and has sufficiently high inhibitive capability against resin decomposition under reduced pressure and high temperature conditions, and thus can, in particular, suitably be compounded in a resin composition that may be subjected to treatment under reduced pressure and high temperature conditions during production, shaping, or the like. Moreover, the presently disclosed resin composition can be efficiently produced by the presently disclosed method of producing a resin composition. Furthermore, the presently disclosed resin composition can suitably be used as a material of the presently disclosed shaped product.

(Phenol Compound)

The presently disclosed phenol compound is a phenol compound that is represented by general formula (I), shown below.

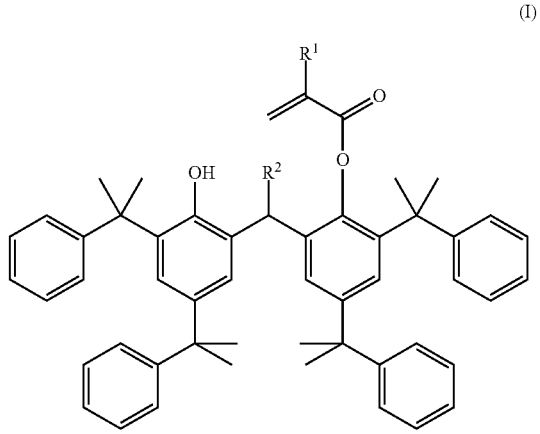

(I)

(In general formula (I), $R^1$ and $R^2$ each indicate, independently of each other, a hydrogen atom or an alkyl group.)

As a result of satisfying the specific structure indicated by general formula (I), the presently disclosed phenol compound does not readily volatilize even upon exposure to high temperature conditions and has sufficiently high inhibitive capability against resin decomposition under high temperature and reduced pressure conditions. Therefore, compounding of this phenol compound in a resin composition makes it possible to sufficiently inhibit resin decomposition even in a situation in which the resin composition is subjected to treatment under reduced pressure and high temperature conditions.

In general formula (I), the alkyl groups of $R^1$ and $R^2$ may, independently of each other, be an alkyl group having a carbon number of 1 to 6, for example. The alkyl group having a carbon number of 1 to 6 may, for example, be an alkyl group having a linear, branched, or cyclic structure such as a methyl group, an ethyl group, a propyl group, a butyl group, a pentyl group, a hexyl group, or a cyclohexyl group without any specific limitations.

In particular, it is preferable that $R^1$ and $R^2$ are each, independently of each other, a hydrogen atom or a methyl group.

More specifically, the phenol compound satisfying the structure indicated by general formula (I) is preferably a phenol compound represented by either of the following formulae (I-1) or (I-2).

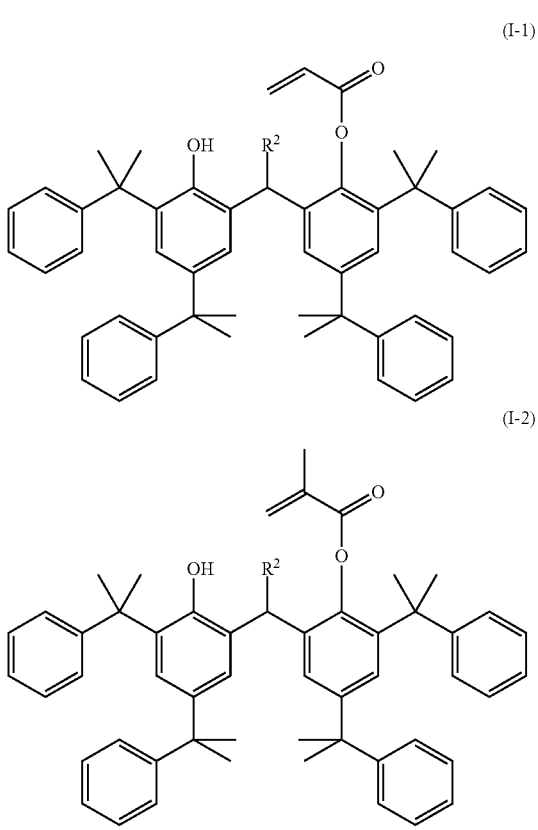

The melting point of the presently disclosed phenol compound is preferably 30° C. or higher, and more preferably 40° C. or higher, and is preferably 200° C. or lower, more preferably 150° C. or lower, and even more preferably 100° C. or lower. When the melting point of the phenol compound is not lower than any of the lower limits set forth above, the phenol compound is a solid at normal temperature, and thus has excellent handleability. Moreover, when the melting point of the phenol compound is not higher than any of the upper limits set forth above, the melting point can easily be kept below the drying temperature, concentrating temperature, or shaping temperature of a resin, the phenol compound is sufficiently easy to melt during production of a shaped product using a resin composition, and the transparency of an obtained shaped product can be increased.

Note that the melting point of a phenol compound can be measured by a method described in the EXAMPLES section.

(Resin Composition)

The presently disclosed resin composition contains a resin and the phenol compound set forth above. As a result of the presently disclosed resin composition containing the phenol compound set forth above, decomposition of the resin can be sufficiently inhibited even in a situation in which the presently disclosed resin composition is subjected to treatment under reduced pressure and high temperature conditions. Note that the resin composition may optionally contain a solvent and additives. Under normal temperature and normal pressure (25° C., 1 atm) conditions, the resin composition may be a solution having the resin dissolved in a solvent or may be a solid material (for example, a resin pellet) that contains the resin in a solid state.

The proportional content of the specific phenol compound set forth above in the resin composition when the content of the resin is taken to be 100 parts by mass is preferably 0.01 parts by mass or more, and more preferably 0.1 parts by mass or more, and is preferably 10 parts by mass or less, and more preferably 1.0 parts by mass or less.

<Resin>

The resin that is contained in the presently disclosed resin composition can be any known polymer depending on the application. Examples of such polymers include the various types of polymers listed as component a) in JP-H3-207788A.

Specific examples include the following.

1. Polymers of monoolefins and diolefins such as polypropylene, polyisobutylene, polybutene, polymethylpentene, polyisoprene, and polybutadiene, as well as polymers of cycloolefins such as polymers of cyclopentene, norbornene, dicyclopentadiene, and tetracyclododecene, and polyethylene (optionally crosslinked) such as high-density polyethylene (HDPE), low-density polyethylene (LDPE), and linear low-density polyethylene (LLDPE)

2. Mixtures of the polymers described above in 1 such as a mixture of polypropylene and polyisobutylene, a mixture of polypropylene and polyethylene (for example, PP/HDPE or PP/LDPE), and a mixture of different types of polyethylene (for example, LDPE/HDPE); copolymers of monoolefins and diolefins as well as copolymers of either or both of a monoolefin and a diolefin with either or both of another vinyl monomer and a cycloolefin, and copolymers of cycloolefins such as ethylene/propylene copolymer, linear low-density polyethylene (LLDPE) and mixtures thereof with low-density polyethylene (LDPE), propylene/butene copolymer, ethylene/hexene copolymer, ethylene/methylpentene copolymer, ethylene/heptene copolymer, ethylene/octene copolymer, propylene/butadiene copolymer, isobutylene/isoprene copolymer, ethylene/alkyl acrylate copolymer, ethylene/alkyl methacrylate copolymer, ethylene/vinyl acetate or ethylene/acrylic acid copolymer and salts thereof (ionomers), as well as terpolymers of ethylene, propylene, and a diene such as hexadiene, dicyclopentadiene, or ethylidene norbornene, ethylene/norbornene copolymer, and ethylene/tetracyclododecene copolymer; and mixtures of such copolymers with one another and with any of the polymers described above in 1 such as polypropylene/ethylene-propylene copolymer, LDPE/EVA, LDPE/EAA, LLDPE/EVA, and LLDPE/EAA 3. Hydrocarbon resins (for example, $C_5$ to $C_9$)

4. Polymers of vinyl aromatics such as polystyrene, poly(p-methylstyrene), poly(α-methylstyrene), polyvinylnaphthalene, and polydiphenylethylene 5. Copolymers of styrene or another vinyl aromatic with a diene or an acrylic derivative such as styrene/butadiene, styrene/isoprene, styrene/acrylonitrile, styrene/alkyl methacrylate, styrene/methylstyrene, styrene/vinylnaphthalene, styrene/methylstyrene/isoprene, styrene/vinylnaphthalene/isoprene, styrene/butadiene/alkyl acrylate, styrene/maleic anhydride, styrene/acrylonitrile/methyl acrylate, impact resistant mixtures produced from a styrene copolymer and another polymer such as a polyacrylate, diene polymer, or ethylene/propylene/diene terpolymer, and block copolymers of styrene such as styrene/butadiene/styrene, styrene/isoprene/styrene, styrene/ethylene/butylene/styrene, and styrene/ethylene/propylene/styrene 6. Graft copolymers of styrene or α-methylstyrene such as a graft copolymer of styrene with polybutadiene, a graft copolymer of styrene with polybutadiene/styrene or polybutadiene/acrylonitrile, a graft copolymer of styrene and acrylonitrile (or methacrylonitrile) with polybutadiene, a graft copolymer of styrene and maleic anhydride or maleimide with polybutadiene, a graft copolymer of styrene, acrylonitrile, and maleic anhydride or maleimide with polybutadiene, a graft copolymer of acrylonitrile and methyl methacrylate with polybutadiene, a graft copolymer of styrene and alkyl acrylate or methacrylate with polybutadiene, a graft copolymer of styrene and acrylonitrile with ethylene/propylene/diene terpolymer, a graft copolymer of styrene and acrylonitrile with polyalkyl acrylate or polyalkyl methacrylate, and a graft copolymer of styrene and acrylonitrile with acrylate/butadiene copolymer, as well as mixtures of any of these graft copolymers with any of the copolymers described above in 5 such as copolymer mixtures known as ABS, MBS, ASA, and AES polymer 7. Halogenated polymers such as polychloroprene, chlorinated rubber, chlorinated or chlorosulfonated polyethylene, a copolymer of ethylene and chlorinated ethylene, and mono and copolymers of epichlorohydrin, with polymers of halogenated vinyl compounds such as polyvinyl chloride, polyvinylidene chloride, polyvinyl fluoride, polyvinylidene fluoride, and copolymers thereof such as vinyl chloride/vinylidene chloride copolymer and vinyl chloride/vinyl acetate or vinylidene chloride/vinyl acetate copolymer being preferable 8. Polymers derived from α,β-unsaturated acids and derivatives thereof such as polyacrylates and polymethacrylates, polyacrylamide, and polyacrylonitrile 9. Copolymers of any of the monomers described above in 8 with one another and copolymers of any of the monomers described above in 8 with other unsaturated monomers such as acrylonitrile/butadiene copolymer, acrylonitrile/alkyl acrylate copolymer, acrylonitrile/alkoxyalkyl acrylate or acrylonitrile/vinyl halide copolymer, and acrylonitrile/alkyl methacrylate/butadiene terpolymer 10. Polymers derived from an unsaturated alcohol and an amine, an acyl derivative, or an acetal thereof such as polyvinyl alcohol, polyvinyl acetate, polyvinyl stearate, polyvinyl benzoate, polyvinyl maleate, polyvinyl butyrate, polyallyl phthalate, and polyallyl melamine; as well as copolymers of any thereof with any of the olefins described above in 1

11. Homopolymers and copolymers of cyclic ethers such as polyalkylene glycol, polyethylene oxide, polypropylene oxide, and copolymers thereof with bisglycidyl ethers 12. Polyacetals such as polyoxymethylene and those polyoxymethylenes that include ethylene oxide as a comonomer; and polyacetals modified with thermoplastic polyurethane, acrylate, or MBS 13. Polyphenylene oxides, polyphenylene sulfides, and polystyrenes; as well as mixtures of at least any one thereof with a polyamide 14. Polyurethanes that are derived from polyethers, polyesters, or polybutadiene with terminal hydroxyl groups and aliphatic or aromatic polyisocyanates, and precursors thereof 15. Polyamides and copolyamides that are derived from a diamine and a dicarboxylic acid and/or from an aminocarboxylic acid or corresponding lactam such as polyamide 4, polyamide 6, polyamide 6/6, 6/10, 6/9, 6/12, and 4/6, polyamide 11, polyamide 12, and aromatic polyamides obtained through condensation of m-xylylenediamine and adipic acid; polyamides produced from hexamethylenediamine and isophthalic acid and/or terephthalic acid, optionally using an elastomer as a modifier, such as poly(2,4,4-trimethyl hexamethylene terephthalamide) and poly(m-phenylene isophthalamide); block copolymers of any of the above-described polyamides with a polyolefin, an olefin copolymer, an ionomer, or a chemically bonded or grafted elastomer, or with a polyether such as polyethylene glycol, polypropylene glycol, or polytetramethylene glycol; and polyamides and copolyamides that are modified using EPDM or ABS 16. Polyureas, polyimides, polyamide-imides, and polybenzimidazole 17. Polyesters that are derived from a dicarboxylic acid and a diol and/or from a hydroxycarboxylic acid or corresponding lactone such as polyethylene terephthalate, polybutylene terephthalate, poly-1,4-dimethylolcyclohexane terephthalate, and polyhydroxybenzoate, as well as block copolyether-esters that are derived from hydroxyl terminal polyethers; and polyesters modified using polycarbonate or MBS 18. Polycarbonates and polyester-carbonates 19. Polysulfones, polyethersulfones, and polyetherketones 20. Unsaturated polyesters that are derived from copolyesters obtained using saturated and unsaturated dicarboxylic acids, polyhydric alcohols, and vinyl compounds as cross-linkers; and halogen-containing modified products of any thereof having low flammability 21. Cross-linkable acrylic resins that are derived from substituted acrylic acid esters such as epoxy acrylates, urethane acrylates, and polyester acrylates 22. Mixtures (polyblends) of any of the polymers described above such as PP/EPDM, polyamide 6/EPDM or ABS, PVC/EVA, PVS/ABS, PVC/MBS, PC/ABS, PBTP/ABS, PC/ASA, PC/PBT, PVC/CPE, PVC/acrylate, POM/thermoplastic PUR, PC/thermoplastic PUR, POM/acrylate, POM/MBS, PPE/HIPS, PPE/PA6.6 and copolymers, PA/HDPE, PA/PP, and PA/PPE 23. Hydrogenated modified products of any of the polymers described above in 1 to 22

Of the various types of polymers listed above, the resin contained in the presently disclosed resin composition is preferably a thermoplastic polymer. In particular, the thermoplastic polymer preferably includes at least any one of a polymer of a vinyl aromatic or hydrogenated modified product thereof; a copolymer of styrene or another vinyl aromatic with a diene; and a block copolymer of styrene. The term "thermoplastic polymer" as used in the present specification refers to a polymer that can display fluidity to an extent that enables shaping upon being heated and that is a polymer for which either or both of a glass-transition point and a melting point can be detected and that softens upon being heated to a temperature equal to or higher than the glass-transition point or melting point.

Note that the polymer described above can be polymerized by any known polymerization method that is suitable for the monomer(s) used to form the polymer without any specific limitations. Moreover, a commercially available polymer may of course be used as the polymer.

<<Weight-Average Molecular Weight of Polymer>>

The weight-average molecular weight of the polymer is preferably 10,000 or more, and more preferably 50,000 or more, and is preferably 1,000,000 or less. When the weight-average molecular weight of the polymer is 10,000 or more, the heat resistance and mechanical strength of a shaped product that is formed from the resin composition can be increased. On the other hand, when the weight-average molecular weight of the polymer is 1,000,000 or less, formability of the resin composition can be increased.

Note that the weight-average molecular weight of a polymer can be measured by a method described in the EXAMPLES section.

<Solvent>

Examples of solvents that can optionally be contained in the presently disclosed resin composition include, but are not specifically limited to, saturated hydrocarbon solvents such as cyclohexane and aromatic hydrocarbon solvents such as toluene. Note that in a case in which the resin composition is in the form of a solution, the content of a solvent in the resin composition can be set as appropriate. Also note that in a case in which the resin composition is a solid material such as a resin pellet, the content of a solvent in the resin composition may be zero (i.e., the resin composition may not substantially contain a solvent).

<Additives>

Other additives may be compounded in the presently disclosed resin composition as necessary. Examples of such additives include heat stabilizers, various types of antioxidants, ultraviolet absorbers, light stabilizers such as hindered amine light stabilizers (HALS), lubricants, nucleating agents, antistatic agents, inorganic fillers, and pigments.

The following provides specific examples of some of these additives.

Examples of heat stabilizers that can be used include 2-tert-butyl-4-methyl-6-(2-hydroxy-3-tert-butyl-5-methylbenzyl)phenyl acrylate (Sumilizer GM) and 1'-hydroxy[2,2'-ethylidenebis[4,6-bis(1,1-dimethylpropyl)benzene]]-1-yl acrylate (Sumilizer GS).

Examples of antioxidants that can be used include, but are not specifically limited to, phenolic antioxidants, phosphoric antioxidants, and sulfuric antioxidants.

Examples of phenolic antioxidants that can be used include butylhydroxytoluene (BHT), 2,2'-methylenebis(6-tert-butyl-p-cresol) (Sumilizer MDP-S), 4,4'-thiobis(6-tert-butyl-m-cresol) (Sumilizer WX-R), 4,4'-butylidenebis(6-tert-butyl-3-methylphenol) (Sumilizer BBM-S), 2,2'-methylenebis(4-ethyl-6-t-butylphenol) (Yoshinox 425), stearyl 3-(3,5-di-tert-butyl-4-hydroxyphenyl)propionate (Irganox 1076), pentaerythritol tetrakis[3-(3,5-di-tert-butyl-4-hydroxyphenyl)propionate] (Irganox 1010), 1,6-hexanediol bis[3-(3,5-di-tert-butyl-4-hydroxyphenyl)propionate] (Irganox 259), 2,2'-thiodiethyl bis[3-(3,5-di-tert-butyl-4-hydroxyphenyl)propionate](Irganox 1035), N,N'-hexamethylene bis[3-(3,5-di-tert-butyl-4-hydroxyphenyl)propanamide] (Irganox 1098), ethylenebis(oxyethylene) bis[3-(3-tert-butyl-4-hydroxy-5-methylphenyl)propionate] (Irganox 245), 2,4,6-tris(3',5'-di-tert-butyl-4'-hydroxybenzyl)mesitylene (Irganox 1330), 1,3,5-tris[[3,5-bis(1,1-dimethylethyl)-4-hydroxyphenyl]methyl]-1,3,5-triazine-2,4,6(1H,3H,5H)-trione (Irganox 3114), 4-[[4,6-bis(octylthio)-1,3,5-triazin-2-yl]amino]-2,6-di-tert-butylphenol (Irganox 565), 2,4-bis(octylthiomethyl)-6-methylphenol (Irganox 1520), 2,4-bis[(dodecylthio)methyl]-6-methylphenol (Irganox 1726), 1,3,5-tris[[4-(1,1-dimethylethyl)-3-hydroxy-2,6-dimethylphenyl]methyl]-1,3,5-triazine-2,4,6(1H,3H,5H)-trione (Cyanox 1790), 2,2'-dimethyl-2,2'-(2,4,8,10-tetraoxaspiro[5.5]undecane-3,9-diyl)dipropane-1,1'-diyl bis [3-(3-tert-butyl-4-hydroxy-5-methylphenyl)propanoate] (Sumilizer GA-80), and 4,4',4''-(1-methylpropanyl-3-ylidene)tris(6-tert-butyl-m-cresol) (Adekastab A-30).

Examples of phosphoric antioxidants that can be used include tris(2,4-di-tert-butylphenyl) phosphite (Irgafos 168), 4,4',4'',4'''-[[(1,1'-biphenyl-4,4'-diyl)bis(phosphinetriyl)]tetrakisoxy]tetrakis(1,3-di-tert-butylbenzene) (Sandostab P-EPQ), 3,9-bis(2,4-di-tert-butylphenoxy)-2,4,8,10-tetraoxa-3,9-diphosphaspiro[5.5]undecane (Ultranox 626), 3,9-bis(2,6-di-tert-butyl-4-methylphenoxy)-2,4,8,10-tetraoxa-3,9-diphosphaspiro[5.5]undecane (Adekastab PEP-36), 2,2'-methylenebis(4,6-di-tert-butylphenyl) 2-ethylhexyl phosphite (Adekastab HP-10), and 2-tert-butyl-6-methyl-4-{3-[(2,4,8,10-tetra-tert-butyldibenzo[d,f][1,3,2]dioxaphosphepin-6-yl)oxy]propyl}phenol (Sumilizer GP).

Examples of sulfuric antioxidants that can be used include dilauryl 3,3'-thiodipropionate (Sumilizer TPL-R), ditetradecyl 3,3'-thiodipropionate (Sumilizer TPM), distearyl-3,3-thiodipropionate (Sumilizer TPS), and 2,2-bis[[3-(dodecylthio)-1-oxopropyloxy]methyl]-1,3-propanediyl bis[3-(dodecylthio)propionate] (Sumilizer TP-D).

Examples of metal deactivators than can be used include N,N'-bis{3-(3,5-di-tert-butyl-4-hydroxyphenyl)propionyl}hydrazine (Irganox MD1024) and [2,2-oxamidobisethyl 3-(3,5-di-tert-butyl-hydroxyphenyl)propionate] (Naugard LX-1).

Examples of ultraviolet absorbers that can be used include drometrizole (Tinuvin P), bumetrizole (Tinuvin 326), 4,6-bis(1,1-dimethylpropyl)-2-(2H-benzotriazol-2-yl)phenol (Tinuvin 328), octrizole (Tinuvin 329), 2-[2-hydroxy-3,5-bis(α,α-dimethylbenzyl)phenyl]-2H-benzotriazole (Tinuvin 234), bisoctrizole (Tinuvin 360), 2,4-di-tert-butylphenyl 3,5-di-tert-butyl-4-hydroxybenzoate (Tinuvin 120), octabenzone (Chimassorb 81), octabenzone (Tinuvin 1577), 2-[4,6-di(2,4-xylyl)-1,3,5-triazin-2-yl]-5-octyloxyphenol (Cyasorb UV-1164), 2-(4,6-diphenyl-1,3,5-triazin-2-yl)-5-[2-(2-ethylhexanoyloxy)ethoxy]phenol (Adekastab LA-46), and 2,4,6-tris(2-hydroxy-4-hexyloxy-3-methylphenyl)-1,3,5-triazine (Adekastab LA-F70).

Examples of HALS that can be used include bis(2,2,6,6-tetramethyl-4-piperidyl) sebacate (Tinuvin 770), bis[1,2,2,6,6-pentamethyl-4-piperidinyl] 2-[[3,5-bis(1,1-dimethylethyl)-4-hydroxyphenyl]methyl]-2-butylpropanedioate (Tinuvin 144), bis[2,2,6,6-tetramethyl-1-(octyloxy)piperidin-4-yl]decanedioate (Tinuvin 123), 1,5,8,12-tetrakis[4,6-bis(N-butyl-N-1,2,2,6,6-pentamethyl-4-piperidylamino)-1,3,5-triazin-2-yl]-1,5,8,12-tetraazadodecane (Tinuvin 119), dimethyl succinate/1-(2-hydroxyethyl)-4-hydroxy-2,2,6,6-tetramethyl-4-piperidine polycondensate (Tinuvin 622), poly[[6-[(1,1,3,3-tetramethylbutyl)amino]-S-triazine-2,4-diyl]-[(2,2,6,6-tetramethyl-4-piperidyl)imino]-hexamethylene-[(2,2,6,6-tetramethyl-4-piperidyl)imino](Chimassorb 944), 1,6-hexanediamine and N,N'-bis(2,2,6,6-tetramethyl-4-piperidinyl)-polymer with 2,4,6-trichloro-1,3,5-triazine and reaction products with N-butyl-1-butanamine and N-butyl-2,2,6,6-tetramethyl-4-piperidinamine (Chimassorb 2020), poly[(6-morpholino-S-triazine-2,4-diyl){2,2,6,6-tetramethyl-4-piperidyl}imino]-hexamethylene[(2,2,6,6-tetramethyl-4-piperidyl)imino] (Cyasorb UV-3346), 1,6-hexanediamine and reaction products of N,N'-bis(2,2,6,6-tetramethyl-4-piperidinyl)-polymer with morpholine-2,4,6-trichloro-1,3,5-triazine (Cyasorb UV-3529), tetrakis(1,2,2,6,6-pentamethyl-4-piperidyl)butane-1,2,3,4-tetracarboxylate (Adekastab LA-52), tetrakis(2,2,6,6-tetramethyl-4-piperidyl)butane-1,2,3,4-tetracarboxylate (Adekastab LA-57), 1,2,3,4-butanetetracarboxylic acid, tetramethyl ester, reaction products with 1,2,2,6,6-pentamethyl-4-piperidinol and β,β,β',β'-tetramethyl-2,4,8,10-tetraoxaspiro[5.5]undecane-3,9-diethanol (Adekastab LA-63P), and 1,2,3,4-butanetetracarboxylic acid, tetramethyl ester, reaction products with 2,2,6,6-tetramethyl-4-piperidinol and β,β,β',β'-tetramethyl-2,4,8,10-tetraoxaspiro[5.5]undecane-3,9-diethanol (Adekastab LA-68).

(Production Method of Resin Composition)

The presently disclosed method of producing a resin composition includes a heating step of heating a mixture containing the above-described resin and the above-described phenol compound to 200° C. or higher under reduced pressure.

More specifically, the heating step may be a step in which impurities that may be unavoidably contained in the mixture and a solvent that is optionally compounded in the mixture are at least partially removed from the mixture and in which the mixture is dried and concentrated to obtain a resin composition in a solution or solid form.

The heating temperature in the heating step is required to be 200° C. or higher, and may be 400° C. or lower. The pressure in the heating step, in terms of absolute pressure, is preferably 50 kPa or lower, and more preferably 20 kPa or lower. In other words, it is preferable that an operation of heating the mixture to 200° C. or higher under a pressure condition of 50 kPa or lower is performed in the heating step.

So long as the temperature condition and pressure condition set forth above are satisfied, the heating step may be implemented by a direct heating and drying method using a commonly known device such as a centrifugal thin-film continuous evaporator, a scraped surface heat exchange continuous reactor-type evaporator, or a high-viscosity reactor without any specific limitations.

Note that prior to the heating step, a step of mixing the above-described resin and the above-described phenol compound to obtain a mixture may be performed. The mixing method is not specifically limited and may be a method in which the specific phenol compound is added to a solution obtained by dissolving the resin and is mixed therewith by a known method.

Moreover, after the heating step, a pelletizing step of pelletizing a melt containing the resin and the specific phenol compound to form a pelletized resin composition may be performed.

(Shaped Product)

The presently disclosed shaped product is obtained through shaping of the resin composition set forth above. As a result of the presently disclosed shaped product containing a resin and the specific phenol compound set forth above, decomposition of the resin (polymer) does not readily proceed even upon exposure to reduced pressure and high temperature conditions, and properties such as mechanical strength can be maintained well. The presently disclosed shaped product can advantageously be used as an optical lens or the like, for example.

The presently disclosed shaped product can be shaped into a film or a shaped product having any of various shapes by a known shaping method that is appropriate based on the desired shape. Examples of shaping methods that can be used include, but are not specifically limited to, injection molding, extrusion molding, and blow molding. Moreover, the shaping method may be a method of processing into the form of non-woven fabric or fiber by melt spinning such as spun bonding or melt blowing. The shaping conditions can be set as appropriate depending on the equipment used in shaping, the desired shape of the shaped product, and so forth.

EXAMPLES

The following provides a more detailed description of the present disclosure through examples. However, the present disclosure is not in any way limited by these examples.

Note that measurements and evaluations in each example were performed by the following methods. Phenol compounds satisfying general formula (I) were produced in accordance with procedures described in Production Examples 1 and 2.

Moreover, in the following description, "parts" and "%" used in expressing quantities are by mass, unless otherwise specified. Furthermore, all pressures mentioned in the following description are absolute pressures.

Measurements of various physical properties and various evaluations were performed by the methods described below.

(1) Evaluation of volatility of test sample and melting point of phenol compound Phenol compounds produced in accordance with Production Examples 1 and 2 and various additives used in Comparative Examples 2 to 4 were each used as a test sample. After 10 mg of the test sample had been loaded into an aluminum pan, the test sample was heated from 30° C. to 300° C. at a heating rate of 15° C./min using a simultaneous thermogravimetric analyzer (TG/DTA; produced by Hitachi High-Tech Science Corporation; product name: STA7200), the weight loss rate at the end of heating was determined, and volatility of the test sample was evaluated in accordance with the following standard.

A: Less than 5%
B: 5% or more

In addition, the melting point of a phenol compound was measured using a melting point system (produced by Mettler Toledo; product name: MP70) with a measurement start temperature of 20° C., a measurement end temperature of 200° C., and a heating rate of 5° C./min. In this manner, the melting points of the phenol compounds produced in accordance with Production Examples 1 and 2 were determined.

(2) Weight-average molecular weight (Mw)

Weight-average molecular weight (Mw) was determined as a standard polystyrene-equivalent value by gel permeation chromatography (GPC) with tetrahydrofuran as an eluent. Standard polystyrene produced by Tosoh Corporation (Mw=589, 1,010, 3,120, 9,490, 13,700, 37,200, 98,900, 189,000, 397,000) was used as the standard polystyrene. An HLC-8020 GPC produced by Tosoh Corporation was used as a measurement apparatus, three columns (TSKgelG5000HXL, TSKgelG4000HXL, and TSKgel G2000HXL) produced by Tosoh Corporation that were linked in series were used as a column, and measurement was performed under conditions of a flow rate of 1.0 mL/min, a sample injection volume of 100 μL, and a column temperature of 40° C.

(3) Evaluation of inhibitive capability against decomposition

Taking the weight-average molecular weight of a polymer at a point before a heating step to be $Mw0$ and the weight-average molecular weight of the polymer at a point after pelletizing to be $Mw1$, a weight-average molecular weight maintenance rate (%) (=$Mw1/Mw0 \times 100$) was determined, and inhibitive capability against polymer decomposition was evaluated in accordance with the following standard for each test sample (phenol compounds produced in accordance with Production Examples 1 and 2 and various additives used in Comparative Examples 2 to 4).

A: 90% or more
B: Not less than 80% and less than 90%
C: Less than 80%

(4) Evaluation of transparency

A haze meter (produced by Nippon Denshoku Industries Co., Ltd.; product name: NDH2000) was used to measure haze (ratio of diffuse transmittance relative to total light transmittance: %) in accordance with JIS K7136:2000 for a shaped product (plate) obtained through shaping of a resin composition obtained in each example or comparative example, and then transparency of the shaped product was evaluated in accordance with the following standard.
A: 0.5% or less
B: More than 0.5% and less than 1.0%
C: 1.0% or more Production Example 1

A four-necked flask including a thermometer and a stirrer was charged with 100 parts of 2,4-bis(α,α-dimethylbenzyl) phenol, 133 parts of xylene, 1.2 parts of dodecyl sulfonic acid, 25 parts of 10% p-toluene sulfonic acid, and 4.3 parts of formaldehyde, was purged with nitrogen, and was then stirred at 110° C. for 4 hours while carrying out a reaction to yield a reaction liquid. Once the reaction was complete, 2,400 parts of xylene was added to the reaction liquid, and the aqueous layer was removed by liquid separation. The organic layer was subsequently washed with water until it become neutral. Next, solvent refluxing was performed under reduced pressure of approximately 200 mmHg at 90° C. to 110° C. while evaporating water to outside of the system. The resultant condensation reaction mixture was cooled, 15.2 parts of triethylamine was subsequently added thereto, and purging with nitrogen was performed. Thereafter, 6.8 parts of acryloyl chloride was added dropwise and a temperature of 40° C. was maintained for 1 hour. The organic layer was subsequently washed with water until it became neutral, and then xylene was evaporated under reduced pressure. Next, methanol was added to this distillation residue and crystallization was performed to yield 87 parts of 2,4-bis(α,α-dimethylbenzyl)-6-[2-hydroxy-3,5-bis(α,α-dimethylbenzyl)]benzylphenyl acrylate (bisphenol monoacrylate compound; hereinafter, also referred to as "phenol compound 1"; represented by following formula). The weight loss rate obtained in evaluation of volatility of the phenol compound 1 as previously described (measurement value according to TG/DTA) was 2.8%. The melting point of the phenol compound 1 was 52° C.

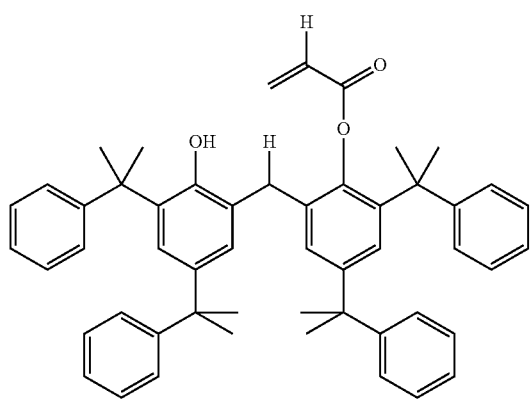 [SMILES: C=CC(=O)Oc1c(Cc2cc(C(C)(C)c3ccccc3)cc(C(C)(C)c3ccccc3)c2O)cc(C(C)(C)c2ccccc2)cc1C(C)(C)c1ccccc1]

Production Example 2

The same operations as in Production Example 1 were performed with the exception that the acryloyl chloride was changed to methacryloyl chloride to thereby yield 2,4-bis(α,α-dimethylbenzyl)-6-[2-hydroxy-3,5-bis(α,α-dimethylbenzyl)]benzylphenyl methacrylate (bisphenol monomethacrylate compound; hereinafter, also referred to as "phenol compound 2"; represented by following formula). The weight loss rate obtained as previously described (measurement value according to TG/DTA) was 2.8%. The melting point of the phenol compound 2 was 57° C.

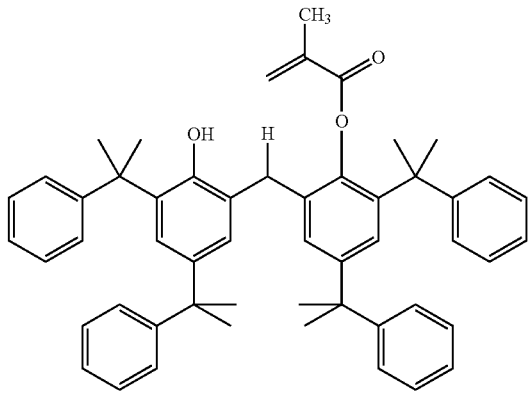 [SMILES: C=C(C)C(=O)Oc1c(Cc2cc(C(C)(C)c3ccccc3)cc(C(C)(C)c3ccccc3)c2O)cc(C(C)(C)c2ccccc2)cc1C(C)(C)c1ccccc1]

Example 1

<Thermoplastic Resin Production Step (Polymerization Through to Hydrogenation)>

A reactor that included a stirrer and had been thoroughly internally purged with nitrogen was charged with 231 parts of dehydrated cyclohexane, 100 parts of dehydrated styrene, and 0.39 parts of dibutyl ether. The whole content of the reactor was stirred at 60° C. while adding 0.53 parts of n-butyllithium (15% cyclohexane solution) to initiate polymerization. Stirring of the whole content was continued at 60° C. for 60 minutes. Next, 0.18 parts of isopropyl alcohol was added to terminate the reaction and thereby yield a polystyrene solution.

The polystyrene solution was transferred to a pressure-resistant reactor including a stirrer, and then 10 parts of nickel catalyst loaded on diatomaceous earth (produced by JGC Catalysts and Chemicals Ltd.; product name: E22U; loaded amount of nickel: 60%) was added as a hydrogenation catalyst and was stirred therewith for 0.1 hours. The inside of the reactor was purged with hydrogen gas, and hydrogen was further supplied into the reactor while stirring the solution to perform a hydrogenation reaction at a temperature of 180° C. and a pressure of 4.6 MPa for 7 hours. This yielded a reaction solution containing hydrogenated polystyrene as a polymer compounded in a resin composition. The weight-average molecular weight (Mw0) of the hydrogenated polystyrene that had been obtained was 90,000.

Next, 0.5 parts of the phenol compound 1 (bisphenol monoacrylate compound) obtained in Production Example 1 was added to the reaction solution and was dissolved therein. This solution was subjected to pressurized filtering (FUNDABAC Filter produced by Ishikawajima-Harima Heavy Industries Co., Ltd.) at a pressure of 0.35 MPa using diatomaceous earth (produced by Showa Chemical Industry Co., Ltd.; product name: Radiolite® #500 (Radiolite is a registered trademark in Japan, other countries, or both)) as a filter bed so as to remove the hydrogenation catalyst and thereby obtain a hydrogenated polystyrene solution that was colorless and transparent.

<Heating Step (Concentrating Step)>

The hydrogenated polystyrene solution was heated to 200° C. in a nitrogen atmosphere and was continuously supplied into a thin-film evaporator (produced by Hitachi, Ltd.; product name: Kontro) at a pressure of 3 MPa. The operating conditions of the thin-film evaporator were set as a pressure of 13.4 kPa and a temperature of 200° C. for the polymer solution concentrated therein. Next, the concentrated solution was continuously withdrawn from the thin-film evaporator and was supplied into a thin-film evaporator of the same type at a pressure of 1.6 MPa. The operating conditions were set as a pressure of 0.5 kPa and a temperature of 260° C.

<Pelletizing Step>

The composition containing the polymer in a molten state was continuously withdrawn from the thin-film evaporator, was extruded from a die at 200° C. inside a class 100 cleanroom, was cooled by water, and was subsequently cut by a pelletizer (product name: OSP-2; produced by Osada Seisakusho) to thereby obtain pellets as a resin composition containing the phenol compound 1 (bisphenol monoacrylate compound) and the hydrogenated polystyrene as a polymer. Mw1 measured after redissolving the pellets in cyclohexane was 86,000.

<Shaping Step>

A small-size kneader (Micro 15 Compounder produced by DSM Xplore) was used to knead and melt the pellets under conditions of 260° C. and 100 rpm for 1 minute, and then a small-size injection molding machine (Micro Injection Moulding Machine 10 cc produced by DSM Xplore) was used to shape a plate of 70 mm in length, 30 mm in width, and 3 mm in thickness under conditions of a shaping temperature of 260° C., an injection pressure of 0.7 MPa, an in-mold holding time of 10 seconds, and a mold temperature of 100° C. The haze of the plate obtained as a shaped product was 0.3%. Various evaluations were performed as previously described based on the various measurement values that were obtained. The results are shown in Table 1.

Example 2

Pellets and a plate were obtained by performing various operations in the same way as in Example 1 with the exception that 0.5 parts of the phenol compound 2 (bisphenol monomethacrylate compound) was added to the reaction solution containing hydrogenated polystyrene as a thermoplastic resin. Mw1 of the pellets was 85,500. The haze of the plate was 0.4%. Various evaluations were performed as previously described based on the various measurement values that were obtained. The results are shown in Table 1.

Comparative Example 1

Pellets and a plate as a shaped product were obtained by performing various operations in the same way as in Example 1 with the exception that the phenol compound 1 was not added after the hydrogenation reaction. Mw1 of the pellets was 60,000. The haze of the plate was 1.1%. Various evaluations were performed as previously described based on the various measurement values that were obtained. The results are shown in Table 1.

Comparative Example 2

Pellets and a plate as a shaped product were obtained by performing various operations in the same way as in Example 1 with the exception that 0.5 parts of Sumilizer GS (produced by Sumitomo Chemical Co., Ltd.; 1'-hydroxy[2,2'-ethylidenebis[4,6-bis(1,1-dimethylpropyl)benzene]]-1-yl acrylate; following formula), which is an additive that does not satisfy the structure indicated in general formula (I), was added to the reaction solution containing hydrogenated polystyrene as a thermoplastic resin. The weight loss rate of the Sumilizer was 12.7%. Mw1 of the pellets was 77,000. The haze of the plate was 0.4%. Various evaluations were performed as previously described based on the various measurement values that were obtained. The results are shown in Table 1.

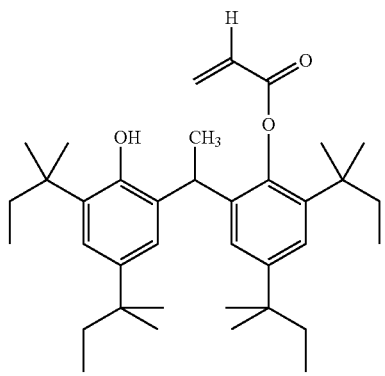 [SMILES: C=CC(=O)Oc1c(C(C)c2cc(C(C)(C)CC)cc(C(C)(C)CC)c2O)cc(C(C)(C)CC)cc1C(C)(C)CC]

Comparative Example 3

Pellets and a plate as a shaped product were obtained by performing various operations in the same way as in Example 1 with the exception that 0.5 parts of Sumilizer GM (produced by Sumitomo Chemical Co., Ltd.; 2-tert-butyl-4-methyl-6-(2-hydroxy-3-tert-butyl-5-methylbenzyl)phenyl acrylate; following formula), which is an additive that does not satisfy the structure indicated in general formula (I), was added to the reaction solution containing hydrogenated polystyrene as a thermoplastic resin. The weight loss rate of the Sumilizer GM was 29.5%. Mw1 of the pellets was 75,000. The haze of the plate was 0.9%. Various evaluations were performed as previously described based on the various measurement values that were obtained. The results are shown in Table 1.

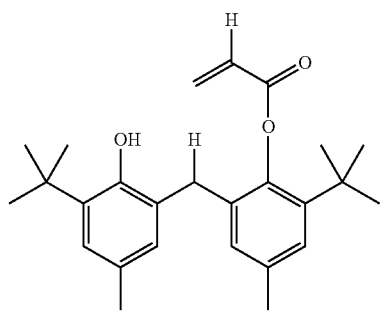 [SMILES: C=CC(=O)Oc1c(Cc2cc(C)cc(C(C)(C)C)c2O)cc(C)cc1C(C)(C)C]

Comparative Example 4

Pellets and a plate as a shaped product were obtained by performing various operations in the same way as in Example 1 with the exception that 0.5 parts of Irganox 1010 (produced by BASF Japan Ltd.; pentaerythritol tetrakis[3-(3,5-di-tert-butyl-4-hydroxyphenyl)propionate]), which is an additive that does not satisfy the structure indicated in general formula (I), was added to the reaction solution containing hydrogenated polystyrene as a thermoplastic resin. Mw1 of the pellets was 64,000. The haze of the plate was 0.4%. Various evaluations were performed as previously described based on the various measurement values that were obtained. The results are shown in Table 1.

TABLE 1

|  |  | Examples | | Comparative Examples | | | |
|---|---|---|---|---|---|---|---|
|  |  | 1 | 2 | 1 | 2 | 3 | 4 |
| Phenol compound satisfying formula (I) | Production example no. | 1 | 2 | — | — | — | — |
|  | $R^1$ | H | $CH_3$ | — | — | — | — |
|  | $R^2$ | H | H | — | — | — | — |
|  | Additive | — | — | — | Sumilizer GS | Sumilizer GM | Irganox 1010 |
| Evaluation | Volatility | A | A | — | B | B | A |
|  | Inhibitive capability against decomposition | A | A | C | B | B | C |
|  | Transparency | A | A | C | A | B | A |

Examples 1 and 2 in Table 1 clearly demonstrate that a bisphenol monoacrylate compound and a bisphenol monomethacrylate compound having a specific structure satisfying general formula (I) did not readily volatilize even upon exposure to high temperature conditions and had sufficiently high inhibitive capability against resin decomposition under reduced pressure and high temperature conditions.

On the hand, it was confirmed through Comparative Example 1 that decomposition of the thermoplastic resin used in Example 1 proceeded upon exposure to vacuum and high temperature conditions in a case in which the specific bisphenol monoacrylate compound or bisphenol monomethacrylate compound was not compounded.

Moreover, it can be seen through Comparative Examples 2 and 3 that additives having a similar structure to the bisphenol monoacrylate compound used in Example 1 but not satisfying general formula (I) had insufficient inhibitive capability against resin decomposition under reduced pressure and high temperature conditions and tended to readily volatilize upon exposure to high temperature conditions.

Furthermore, it can be seen through Comparative Example 4 that although an antioxidant (Irganox 1010) having a clearly different structure to the bisphenol monoacrylate compound used in Example 1 did not readily volatilize under high temperature conditions, the antioxidant had insufficient inhibitive capability against resin decomposition under reduced pressure and high temperature conditions.

Also note that Examples 1 and 2 each had an evaluation result of "A" for transparency. This indicates that a bisphenol monoacrylate compound and a bisphenol monomethacrylate compound having a specific structure satisfying general formula (I) could inhibit resin coloring well upon exposure to high temperature conditions.

INDUSTRIAL APPLICABILITY

According to the present disclosure, it is possible to provide a phenol compound that does not readily volatilize even upon exposure to high temperature conditions and that has sufficiently high inhibitive capability against resin decomposition under reduced pressure and high temperature conditions.

Moreover, according to the present disclosure, it is possible to provide a resin composition containing this phenol compound and an efficient production method for the resin composition.

Furthermore, according to the present disclosure, it is possible to provide a shaped product formed of the resin composition.

The invention claimed is:

1. A phenol compound represented by general formula (I), shown below,

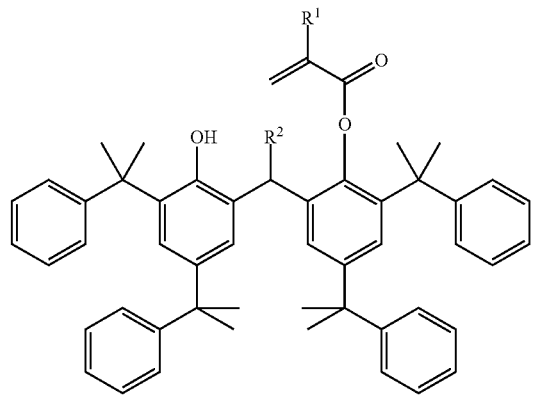

(I)

where, in general formula (I), $R^1$ and $R^2$ each indicate, independently of each other, a hydrogen atom or an alkyl group.

2. The phenol compound according to claim 1, wherein $R^1$ and $R^2$ in general formula (I) are each a hydrogen atom.

3. The phenol compound according to claim 1, wherein $R^1$ in general formula (I) is a methyl group and $R^2$ in general formula (I) is a hydrogen atom.

4. A resin composition comprising: a resin; and the phenol compound according to claim 1.

5. The resin composition according to claim 4, wherein the resin is a thermoplastic polymer.

6. A shaped product obtained through shaping of the resin composition according to claim 4.

7. A method of producing the resin composition according to claim 4, comprising a heating step of heating a mixture containing the resin and the phenol compound to 200° C. or higher under reduced pressure.

* * * * *